(12) United States Patent
Bagwell, Sr.

(10) Patent No.: US 9,706,917 B1
(45) Date of Patent: Jul. 18, 2017

(54) EYE EXAMINATION TEMPLATE

(71) Applicant: Don C. Bagwell, Sr., Columbus, GA (US)

(72) Inventor: Don C. Bagwell, Sr., Columbus, GA (US)

( * ) Notice: Subject to any disclaimer, the term of this patent is extended or adjusted under 35 U.S.C. 154(b) by 0 days.

(21) Appl. No.: 15/079,182

(22) Filed: Mar. 24, 2016

(51) Int. Cl.
*A61B 3/10* (2006.01)
*A61B 3/12* (2006.01)

(52) U.S. Cl.
CPC ............. *A61B 3/12* (2013.01); *A61B 3/1005* (2013.01)

(58) Field of Classification Search
CPC . G06T 7/11; G06T 11/203; A61B 3/12; A61B 3/14; A61B 3/0041
USPC ....................................... 351/211
See application file for complete search history.

(56) References Cited

U.S. PATENT DOCUMENTS

| | | | |
|---|---|---|---|
| 4,526,449 A | 7/1985 | Newman et al. | |
| 4,998,818 A | 3/1991 | Kugler et al. | |
| 5,396,303 A | 3/1995 | Peters et al. | |
| 5,615,683 A | 4/1997 | Toge et al. | |
| 5,830,147 A | 11/1998 | Feke et al. | |
| 6,276,799 B1 | 8/2001 | Van Saarloos et al. | |
| 7,055,955 B2 | 6/2006 | Kishida et al. | |
| 7,524,064 B2 | 4/2009 | Wyatt | |
| 7,744,221 B2 | 6/2010 | Wei et al. | |
| 7,992,999 B2 | 8/2011 | Xu et al. | |
| 8,405,834 B2 | 3/2013 | Srinivasan et al. | |
| 8,474,978 B2 | 7/2013 | Huang et al. | |
| 8,705,826 B2 | 4/2014 | Liu et al. | |
| 9,101,293 B2 | 8/2015 | Everett et al. | |
| 2013/0110093 A1 | 5/2013 | Yee | |
| 2015/0187070 A1 | 7/2015 | Cheng et al. | |

FOREIGN PATENT DOCUMENTS

CA 2000747 4/1991

OTHER PUBLICATIONS

Eye Wiki; Article entitled: "Smart Phoneography—How to take slit lamp photographs with an iPhone", available at <http://eyewiki.aao.org/Smart_Phoneography_-_How_to_take_slit_lamp_photographs_with_an_iPhone>, accessed on Mar. 23, 2016, 12 pgs.
Sing, et al.; Article entitled: "The Normal Optic Nerve Head", Optometry and Vision Science, vol. 77, No. 6, Jun. 2000, 9 pgs.
Timberlake, et al.; Article entitled: "The Direct Ophthalmoscope—How it Works and How to Use it", University of Kansas, 2005, 39 pgs.

(Continued)

*Primary Examiner* — Mahidere Sahle
(74) *Attorney, Agent, or Firm* — Taylor English Duma LLP (57) ABSTRACT

An eye examination template for measuring an optic disc can include an x-axis measurement line, a y-axis measurement line, and an optic disc oval. In one aspect, the x-axis measurement line can include a plurality of x-axis measurement marks. In another aspect, the y-axis measurement line can include a plurality of y-axis measurement marks. In yet another aspect, the y-axis measurement line can intersect the x-axis measurement line at a square angle intersection. In a further aspect, the optic disc oval can be centered on the intersection of the y-axis measurement line with the x-axis measurement line. In one aspect, the optic disc oval can correspond with an average optic disc size of a first demographic of a population.

20 Claims, 6 Drawing Sheets

(56) References Cited

OTHER PUBLICATIONS

Welch Allyn; Article entitled: "3.5V Coaxial Ophthalmoscope", located at <http://intl.welchallyn.com/apps/products/product.jsp?id=11-ac-100-0000000001136>, accessed on Oct. 20, 2015, 2 pgs.
Welch Allyn; Brochure entitled: "A Guide to the Use of Diagnostic Instruments in Eye and Ear Examinations", Copyright 2006, 17 pgs.
Welch Allyn; User Manual for Ophthamoscopes, Otoscopes and No. 20000 Otoscope/Throat Illuminator, publicly available prior to Mar. 23, 2016, 2 pgs.

EYE EXAMINATION TEMPLATE

BACKGROUND

Field

This application relates generally to an eye examination template. More particularly, embodiments of the subject matter relate to an eye examination template for observing and measuring an optic disc or other features of a fundus of an eye.

Background Technology

Generally, a human eye has an anterior segment and a posterior segment that is a front and a back of the eye, respectively. The main structures of the anterior segment include, but are not limited to, a cornea, an iris, and a lens. A pupil of the eye is a "window" to the posterior segment. The pupil is an opening in a center of the iris, and the larger the pupil the easier it is to view the back of the eye (the posterior segment) and view an inside of the back of the eye. The inside of the back of the eye is otherwise known as the fundus of the eye. The fundus includes, but is not limited to, a retina, an optic disc, and a macula. Generally, the retina is a light-sensitive layer of tissue that forms nerve impulses that, once received and processed by the brain, form visual images.

The nerve impulses are sent to the back of the brain (the visual cortex located in the occipital lobe) via an optic nerve and an optic tract. The optic disc is a point of exit for neurons leaving the eye representing the beginning of the optic nerve, and is also is an entry point for blood vessels to and from the retina. The optic disc can comprise a central depression therein, which is commonly known as a cup. This cup can be associated with the degenerative disease glaucoma.

Eye specialists and other professionals commonly observe the fundus of the eye through visual examination or photography to detect and observe various medical signs, such as hemorrhages, exudates, cotton wool spots, blood vessel abnormalities, lesions, and pigmentation. Observation of various characteristics of the fundus can also be used to diagnose various other medical conditions. For example and without limitation, a ratio of a size of the cup to a size of the optic disc, which is commonly known as the cup-to-disc ratio, can be used to diagnose glaucoma.

Despite the benefits, variability in the eye's anatomy and variability in an examiner's judgment reduce the overall reliability and effectiveness of eye examinations of the fundus. In particular, because the anatomy of the eye can vary from person to person depending on various factors such as race, gender, and other demographic characteristics, diseases, etc., there will be variations in what a "normal" eye should look like. Furthermore, because most routine eye examinations rely on observational judgment and estimation of the examiner, which are based on experience and other human factors that can vary from examiner to examiner, a judgment or estimate made by one examiner is not necessarily the same judgment that will be reached by a different examiner.

It is with respect to these and other considerations that the disclosure made herein is presented.

SUMMARY

Described herein is an eye examination template for measuring an optic disc and a method of examining an optic disc and a cup of an eye. The eye examination template is configured for use with scopes, lamps, cameras, and various other instruments that can be utilized for viewing a patient's eye. In one aspect, the eye examination template can comprise an x-axis measurement line comprising a plurality of x-axis measurement marks. In one aspect, each one of the plurality of x-axis measurement marks can be spaced apart at a first distance from an adjacent one of the plurality of x-axis measurement marks. In a further aspect, the eye examination template can comprise a y-axis measurement line intersecting the x-axis measurement line at a square angle intersection. In one aspect, the y-axis measurement line can comprise a plurality of y-axis measurement marks. Each one of the plurality of y-axis measurement marks can be spaced apart at a second distance from an adjacent one of the plurality of y-axis measurement marks. In another aspect, the eye examination template can comprise an optic disc oval centered on the intersection of the y-axis measurement line with the x-axis measurement line. In one aspect, the optic disc oval can correspond with an average optic disc size of a first demographic of a population.

In another aspect, a system for examining an optic disc of an eye can comprise an eye examination instrument configured to view a back of the eye and the eye examination template. In one aspect, the eye examination template can be configured to be projected onto the back of the eye through the eye examination instrument.

In a further aspect, the method of examining an optic disc and the cup of the eye can comprise projecting the eye examination template on a back of the eye. In a further aspect, the method can comprise aligning the optic disc oval of the eye examination template on the optic disc of the eye.

Various implementations described in the present disclosure can include additional systems, methods, features, and advantages, which can not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

DETAILED DESCRIPTION

The present invention can be understood more readily by reference to the following detailed description, examples, drawings, and claims, and the previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a band" can include two or more such bands unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or can not occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "can," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment. Directional references such as "up," "down," "top," "left," "right," "front," "back," and "corners," among others are intended to refer to the orientation as illustrated and described in the figure (or figures) to which the components and directions are referencing.

Figure 1:
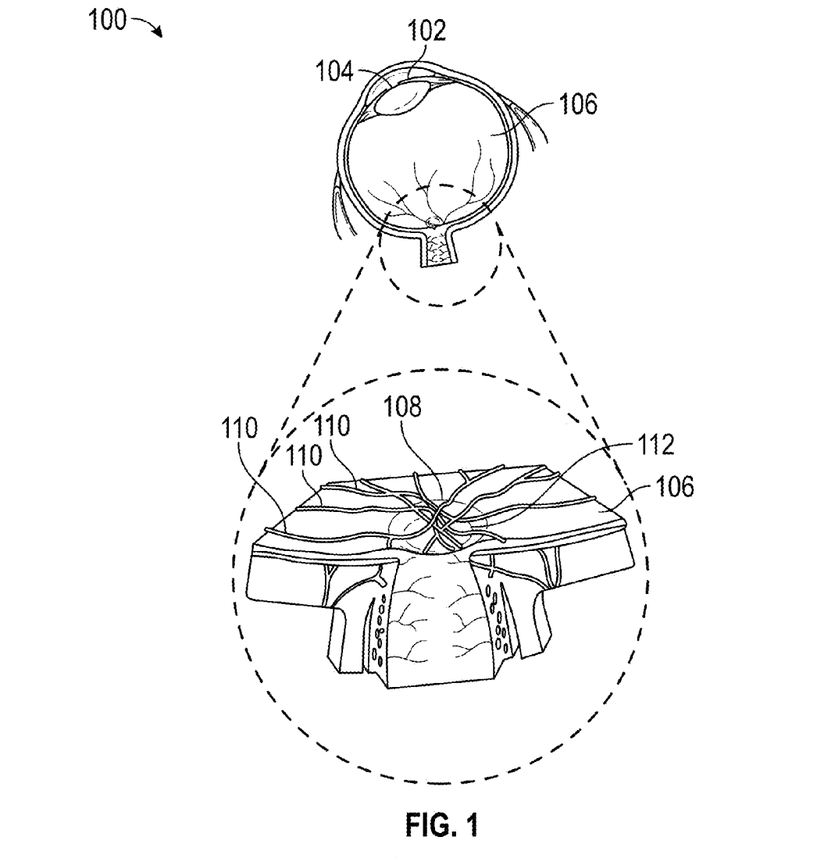
FIG. 1 is a diagram of a generic eye.

A non-limiting example of a generic eye 100 is shown in FIG. 1. Generally, an iris 102 and a pupil 104 are components at the front of the eye 100 and a retina 106 and an optic disc 108 are components at the back, or fundus, of the eye 100. The pupil 104 is a hole in the center of the iris 102 that allows light to strike the retina 106. The iris 102 is a circular structure responsible for controlling the size of the pupil 104, which controls the amount of light that can reach the retina 106. Generally, the retina 106 is a light-sensitive layer of tissue that receives the visual image and in turn creates chemical and electrical events triggering nerve impulses. The nerve impulses are sent to the visual cortex of the brain via an optic nerve and the optic tract. The optic disc 108 is a portion on the retina 106 and is a point of exit for neurons leaving the eye 100. The optic disc 108 represents the beginning of the optic nerve. The optic disc 108 also is an entry point for blood vessels 110 for the retina 106. The optic disc 108 can comprise a central depression, which is commonly known as a cup 112.

Figure 2:
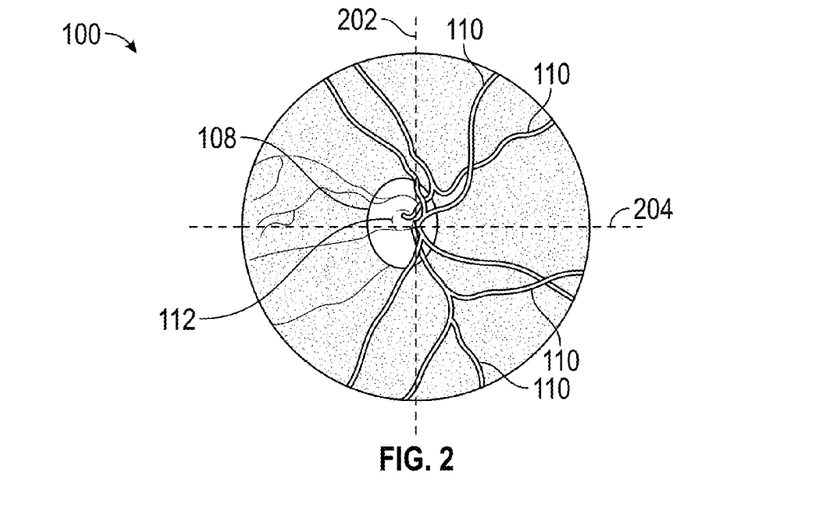
FIG. 2 is a view of a back of an eye showing an optic disc and a cup.

FIG. 2 shows a view of the fundus of the eye 100. As shown in FIG. 2, typically, the optic disc 108 and the cup 112 are slightly oval with a diameter in a vertical direction 202 greater than a diameter in a horizontal direction 204, respectively.

Figure 3:
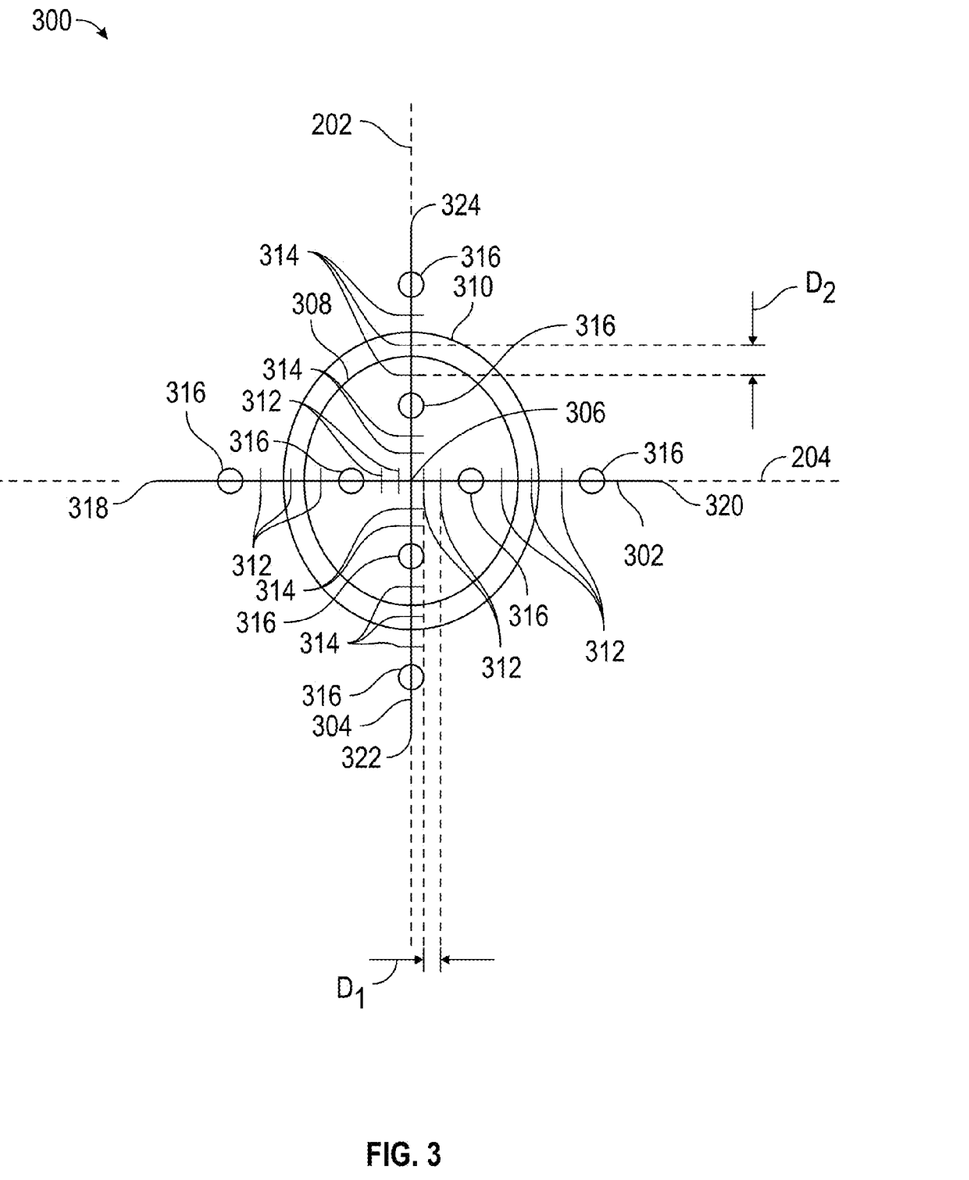
FIG. 3 is a front view of an eye examination template in accordance with one aspect of the current disclosure.

Referring to FIG. 3, in one aspect, disclosed is an eye examination template 300 and associated methods, systems, devices, and various apparatus. The eye examination template 300 can be an aperture or lens with the template 300 placed on or in the lens in such a way that the template 300 is projected on the back of the eye. The eye examination template 300 can be configured to be used with various instruments for viewing the fundus of the eye 100. For example and without limitation, the eye examination template 300 can be configured to be used with an ophthalmoscope 502 (shown in FIGS. 5-6B), a slit lamp 700 (shown in FIG. 7), various other scopes, fundus photography devices, adapters for various scopes and devices for viewing the fundus of the eye 100, or various other devices that can be used to view the fundus of the eye 100. In this aspect, the eye examination template 300 can be projected onto the fundus of the eye 100 through the various eye examination instruments.

In one aspect, the eye examination template 300 can comprise an x-axis measurement line 302 and a y-axis measurement line 304. Referring to FIG. 3, the x-axis measurement line 302 can have a first end 318 and a second end 320 distal from the first end 318. Similarly, the y-axis measurement line 304 can have a first end 322 and a second end 324 distal from the first end 322. It is contemplated that the y-axis measurement line 304 can intersect the x-axis measurement line 302 at a square angle intersection 306. In one aspect, the intersection 306 can be at a midpoint of the x-axis measurement line 302 and a midpoint of the y-axis measurement line 304. In one aspect, the intersection 306 can be an effective intersection where the y-axis measurement line 304 and x-axis measurement line 302 effectively cross, even if the intersection 306 itself is not visible, as shown for example in FIG. 4.

In another aspect, the eye examination template 300 can comprise a first optic disc oval 308. In one aspect, the first optic disc oval 308 can be centered on the intersection 306 of the x-axis measurement line 302 with the y-axis measurement line 304. As shown, the first optic disc oval 308 can have a diameter in the vertical direction 202 that is greater than a diameter in the horizontal direction 204 to correspond with the general shape of the optic disc 108. Optionally, in one aspect, a distance from the first end 318 to the second end 320 of the x-axis measurement line 302 is greater than the diameter of the first optic disc oval 308 in the horizontal direction 204 and a distance from the first end 322 to the second end 324 of the y-axis measurement line 304 is greater than the diameter of the first optic disc oval 308 in the vertical direction 202. The x-axis measurement line 302 and the y-axis measurement line 304 thereby extend completely through the first optic disc oval 308 and beyond a perimeter of the first optic disc oval 308.

In one aspect, the first optic disc oval 308 can be dimensioned to correspond with an average optic disc size of a demographic of the population. For example and without limitation, it is contemplated that the demographic can be race (e.g. American Indian, Asian, African-American, Caucasian, Pacific Islander, Hispanic, etc.), gender (e.g. male, female, etc.), age, or various other demographics of the population or combinations thereof. As a non-limiting example, the first optic disc oval 308 can be dimensioned to correspond with the average optic disc size of a male. It is also contemplated that the first optic disc oval 308 can correspond with the average optic disc size of multiple demographics of the population. As a non-limiting example, the first optic disc oval 308 can be dimensioned to correspond with the average optic disc size of a female African-American person. It is contemplated that various other demographic combinations can be present.

Optionally, the eye examination template 300 can comprise a second optic disc oval 310. In one aspect, the second optic disc oval 310 can be centered on the intersection 306 of the x-axis measurement line 302 with the y-axis measurement line 304. Similar to the first optic disc oval 308, the second optic disc oval 310 can have a diameter in the vertical direction 202 be greater than a diameter in the horizontal direction 204 to correspond with the general shape of the optic disc 108. Optionally, in one aspect, the distance from the first end 318 to the second end 320 of the x-axis measurement line 302 is greater than the diameter of the second optic disc oval 310 in the horizontal direction 204 and the distance from the first end 322 to the second end 324 of the y-axis measurement line 304 is greater than the diameter of the second optic disc oval 310 in the vertical direction 202. The x-axis measurement line 302 and the y-axis measurement line 304 thereby extend completely through the second optic disc oval 310 and beyond a perimeter of the second optic disc oval 310.

Similar to the first optic disc oval 308, the second optic disc oval 310 can be dimensioned to correspond with an average optic disc size of a demographic of the population or any combination thereof. In one aspect where the second optic disc oval 310 is utilized, the first optic disc oval 308 can correspond with an average optic disc size of a first demographic of the population and the second optic disc oval 310 can be dimensioned to correspond with a second demographic of the population, where the first demographic and the second demographic have different average optic disc sizes. As one non-limiting example, the first optic disc oval 308 can be dimensioned to correspond with the average optic disc size of a male and the second optic disc oval 310 can be dimensioned to correspond with the average optic disc size of a female. As another non-limiting example, the first optic disc oval 308 can be dimensioned to correspond with the average optic disc size of a Caucasian male and the second optic disc oval 310 can be dimensioned to correspond with the average optic disc size of an African-American male. It is contemplated that various other demographic combinations can be present.

Depending on the demographic used to dimension the second optic disc oval 310, the diameter of the second optic disc oval 310 in the vertical direction 202 can be greater than or less than the diameter of the first optic disc oval 308 in the vertical direction 202. Similarly, the diameter of the second optic disc oval 310 in the horizontal direction 204 can be greater than or less than the diameter of the first optic disc oval 308 in the horizontal direction 204. In this aspect, depending on the demographics used for the optic disc ovals 308,310, respectively, either the second optic disc oval 310 can encircle the first optic disc oval 308 or the first optic disc oval 308 can encircle the second optic disc oval 310. In the aspect shown in FIG. 3, and the first optic disc oval 308 is an inner optic disc oval and the second optic disc oval 310 is an outer optic disc oval. It is also contemplated that in another aspect, the eye examination template 300 can comprise a plurality of optic disc ovals corresponding to the average optic disc sizes of various demographics of the population. Accordingly, one having skill in the art will appreciate that the number of optic disc ovals should not be considered limiting on the current disclosure as it is contemplated that at least the first optic disc oval 308 can be present.

In one aspect, the x-axis measurement line 302 can comprise a plurality of x-axis measurement marks 312 between the first end 318 and the second end 320. The number of x-axis measurement marks 312 should not be considered limiting on the current disclosure as it is contemplated that any number of x-axis measurement marks 312 can be present. Optionally, the x-axis measurement line 302 can comprise an equal number of x-axis measurement marks 312 on either side of the intersection 306 with the y-axis measurement line 304. As a non-limiting example, the x-axis measurement line 302 can comprise six x-axis measurement marks 312 between the intersection 306 and the first end 318 and six x-axis measurement marks 312 between the intersection 306 and the second end 320 for a total of twelve x-axis measurement marks 312. As another non-limiting example, the x-axis measurement line 302 can comprise five x-axis measurement marks 312 between the intersection 306 and the first end 318 and five x-axis measurement marks 312 between the intersection 306 and the second end 320 for a total of ten x-axis measurement marks 312. In one aspect, each one of the plurality of x-axis measurement marks 312 can be spaced apart from an adjacent one of the plurality of x-axis measurement marks 312 at a first distance $D_1$.

Similarly, the y-axis measurement line 304 can comprise a plurality of y-axis measurement marks 314 between the first end 322 and the second end 324. The number of y-axis measurement marks 314 should not be considered limiting on the current disclosure as it is contemplated that any number of y-axis measurement marks 314 can be present. Similar to the x-axis measurement line 302, the y-axis measurement line 304 can optionally comprise an equal number of y-axis measurement marks 314 on either side of the intersection 306 with the x-axis measurement line 302. As a non-limiting example, the y-axis measurement line 304 can comprise five y-axis measurement marks 314 between the intersection 306 and the first end 322 and five y-axis measurement marks 314 between the intersection 306 and the second end 324 for a total of ten y-axis measurement marks 314. In one aspect, it is contemplated that the eye examination template 300 can optionally comprise an equal number of x-axis measurement marks 312 and y-axis measurement marks 314. In another aspect, each one of the plurality of y-axis measurement marks 314 can be spaced apart from an adjacent one of the plurality of y-axis measurement marks 314 at a second distance $D_2$. It is contemplated that the second distance $D_2$ is different from the first distance $D_1$.

Because the optic disc ovals 308,310 have diameters greater in the vertical direction 202 compared to the horizontal direction 204 (instead of being circular), respectively, the second distance $D_2$ can be greater than the first distance $D_1$. In this aspect, the second distance $D_2$ can be the first distance $D_1$ multiplied by some predetermined number. In this aspect, the optic disc ovals 308,310 can respectively intersect the x-axis measurement line 302 and y-axis measurement line 304, respectively, at the same measurement mark on the respective lines 302,304. As a non-limiting example, the first optic disc oval 308 can intersect the x-axis measurement line 302 at the fourth x-axis measurement mark 312 on either side of the intersection 306 as measured from the intersection 306 and can intersect the y-axis measurement line 304 at the fourth y-axis measurement mark 314 on either side of the intersection 306 as measured from the intersection 306. However, because the y-axis measurement marks 314 are spaced at intervals of the second distance $D_2$ and the x-axis measurement marks 312 are spaced at intervals of the first distance $D_1$, the actual distance from the intersection 306 to the fourth y-axis measurement marks 314, respectively, is greater than the actual distance from the intersection 306 to the x-axis measurement marks 312, respectively. Each distance $D_1$, $D_2$, can equal a set percentage of the diameters in the horizontal direction 204 and the vertical direction 202, respectively, of a one or both of the first disc oval 308 or the second disc oval 310. As a non-limiting example, the distances $D_1$, $D_2$, can equal 10% of the respective diameters of the first optic disc oval 308, thereby having eight x-axis measurement marks 312 and eight y-axis measurement marks 314 within the first disc oval 308, with four marks 312,314 on each side of the intersection 306. Additionally, where the first disc oval 308 or the second disc oval 310 intersects the x-axis measurement line 302 or the y-axis measurement line 304 at an x-axis measurement mark 312 or a y-axis measurement mark 314, respectively, the marks can optionally comprise portions of the first disc oval 308 or the second disc oval 310 intersecting the lines 302,304 rather than comprise separate straight lines. The distances $D_1$ and $D_2$ can be as large or as small as needed. For example, larger distances $D_1$ and $D_2$ might be adequate for documenting changes in cup size for most eye care providers but glaucoma specialists can optionally require much smaller distances $D_1$ and $D_2$ and glaucoma researchers can optionally require even smaller distances $D_1$ and $D_2$.

Figure 4:
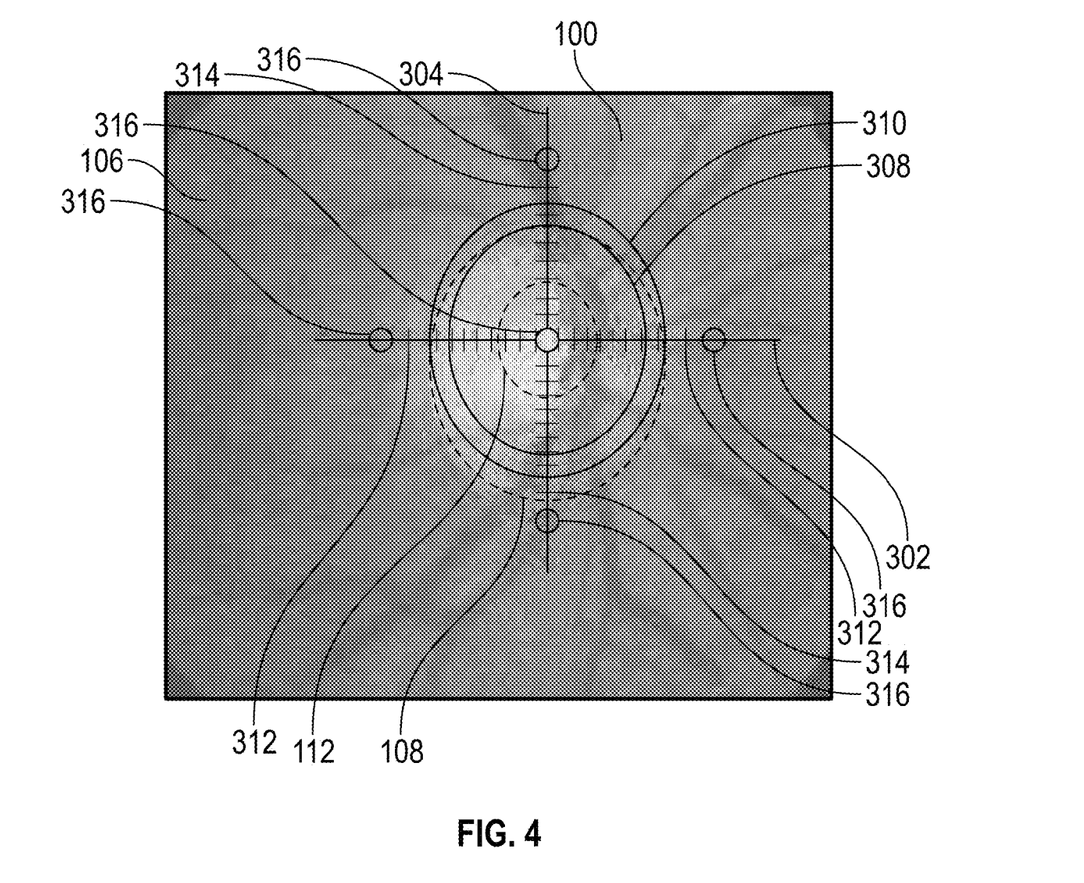
FIG. 4 is a view of the eye examination template of FIG. 3 projected onto an optic disc of an eye.

Optionally, the eye examination template 300 can comprise a plurality of focus circles 316. The number of focus circles 316 should not be considered limiting on the current disclosure as it is contemplated that any number of focus circles 316 can be present. In one aspect, the focus circles 316 can be positioned at various positions along the x-axis measurement line 302, the y-axis measurement line 304, or both, such as shown in FIG. 3 with four focus circles 316 within the first optic disc oval 308 and four focus circles 316 outside of the second optic disc oval 310. Optionally, as shown in FIG. 4, a focus circle 316 can be placed at the intersection 306 such that the intersection 306 is not visible and the x-axis measurement line 302 and the y-axis measurement line 304 effectively intersect. As a non-limiting example, the eye examination template 300 can comprise one focus circle 316 at the intersection 306 of the x-axis measurement line 302 with the y-axis measurement line 304, one focus circle 316 on the x-axis measurement line 302 proximate to the first end 318, one focus circle 316 on the x-axis measurement line 302 proximate to the second end 320, one focus circle 316 on the y-axis measurement line 304 proximate to the first end 322, and one focus circle 316 on the y-axis measurement line 304 proximate to the second end 324. It is also contemplated that the focus circles 316 can be positioned at other locations on the eye examination template 300. In this manner, one having skill in the art will appreciate that the location of the focus circles 316 should not be considered limiting on the current disclosure. Additionally, where any of the focus circles 316 intersect the x-axis measurement line 302 or the y-axis measurement line 304 at an x-axis measurement mark 312 or a y-axis measurement mark 314, respectively, the marks can optionally comprise portions of the focus circle 316 intersecting the lines 302,304 rather than comprise separate straight lines. The x-axis measurement line 302 and the y-axis measurement line 304 can optionally be constructed without focus circles 316 or with just one focus circle 316 at intersection 306. If not placed on the x-axis measurement line 302 or the y-axis measurement line 304, the focus circles 316 could optionally be placed along sides of the x-axis measurement line 302 or the y-axis measurement line 304, as well as out in the general field of view. The latter configuration could be useful to quantify areas of edema and or to define the margins of retinal lesions.

It is contemplated that the focus circles can be configured to ensure that the eye examination template 300, including the measurement lines 302,304, the optic disc ovals 308,310, and the measurement marks 312,314, is focused on the fundus of the eye 100. In this aspect, the focus circles 316 can be dimensioned to be a smallest size that a human eye can identify as a circle and not a blur spot when properly in focus.

Referring to FIG. 4, the eye examination template 300 can be projected onto the fundus of the eye 100 such that the intersection 306 is centered on a center of the optic disc 108 or the cup 112. In another aspect, the eye examination template 300 can be projected onto the fundus of the eye 100 such that the first optic disc oval 308 is aligned on the optic disc 108. The optic disc 108 can be aligned with the first optic disc oval 308 by centering the first optic disc oval 308 on the optic disc 108 or positioning one or multiple edges of the optic disc 108 over an edge of the first optic disc oval 308 or any other position to allow measurement of a difference in size between the first optic disc oval 308 and the optic disc 108. As shown in an exemplary aspect in FIG. 4, a top edge of the optic disc 108 is aligned with a top edge of the first optic disc oval 308, thereby allowing a difference in vertical diameter to be measured along the y-axis measurement line 304 with the y-axis measurement marks 314. In yet another aspect, the eye examination template 300 can be projected onto the fundus of the eye 100 such that the second optic disc oval 310 is aligned on the optic disc 108.

Figure 5:
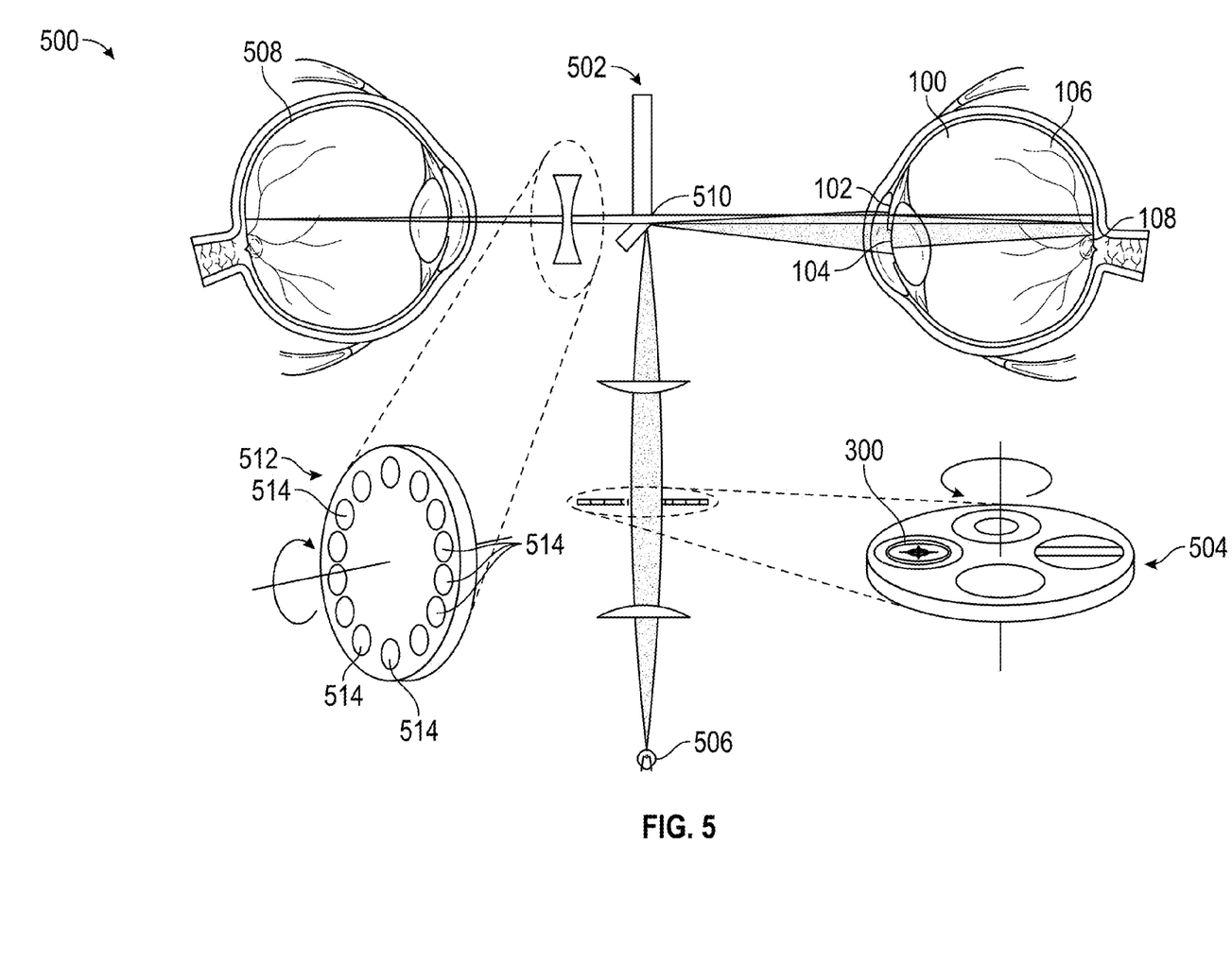
FIG. 5 is a diagram of a system for examining an optic disc of an eye with the eye examination template of FIG. 3 and an eye examination instrument.
Figure 6A:
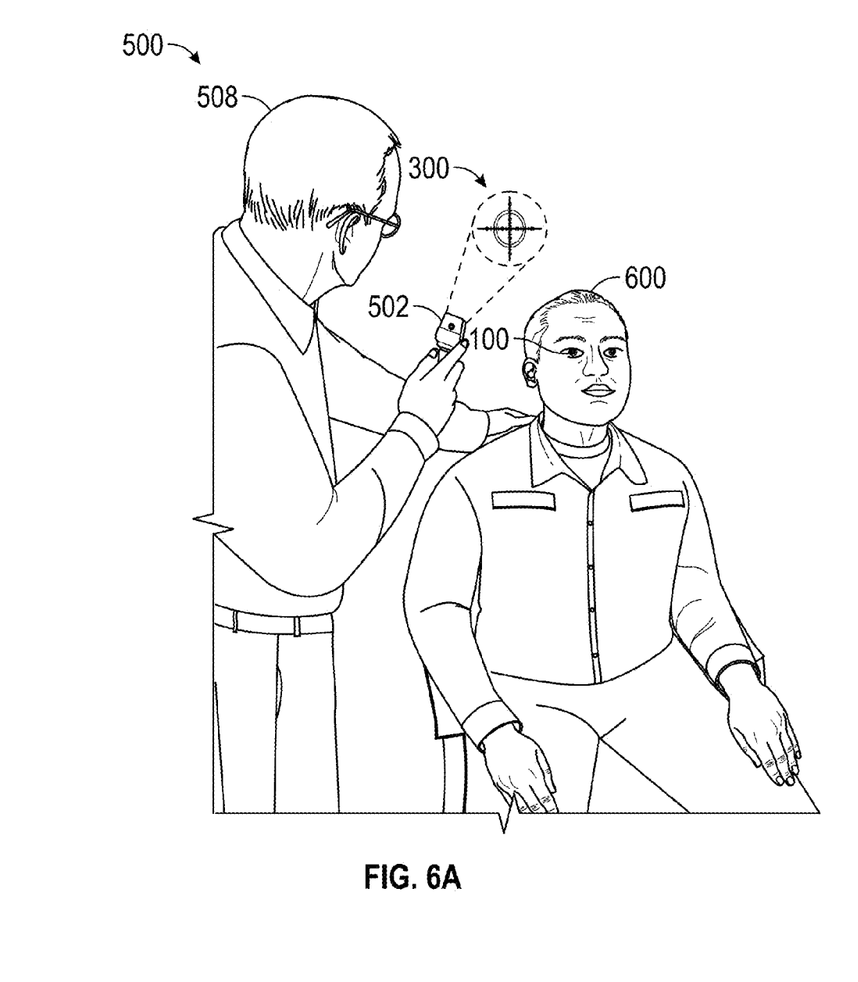
FIG. 6A is a perspective view of an examiner using the system of FIG. 5 to project the eye examination template of FIG. 3 on a wall behind a patient when the eye examination instrument is an ophthalmoscope.
Figure 6B:
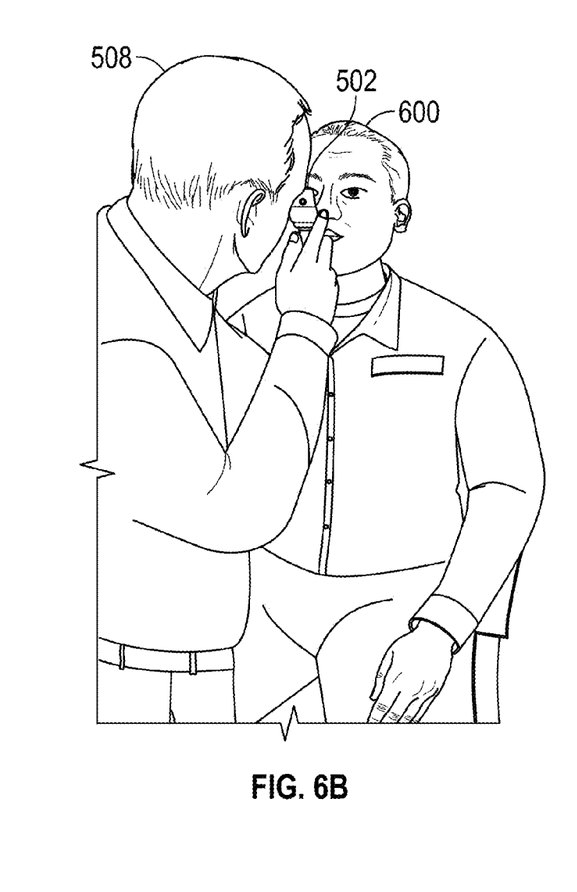
FIG. 6B is another perspective view of the system of FIG. 6A showing the examiner using the system of FIG. 5 on the patient to examine the patient's eye.
Figure 7:
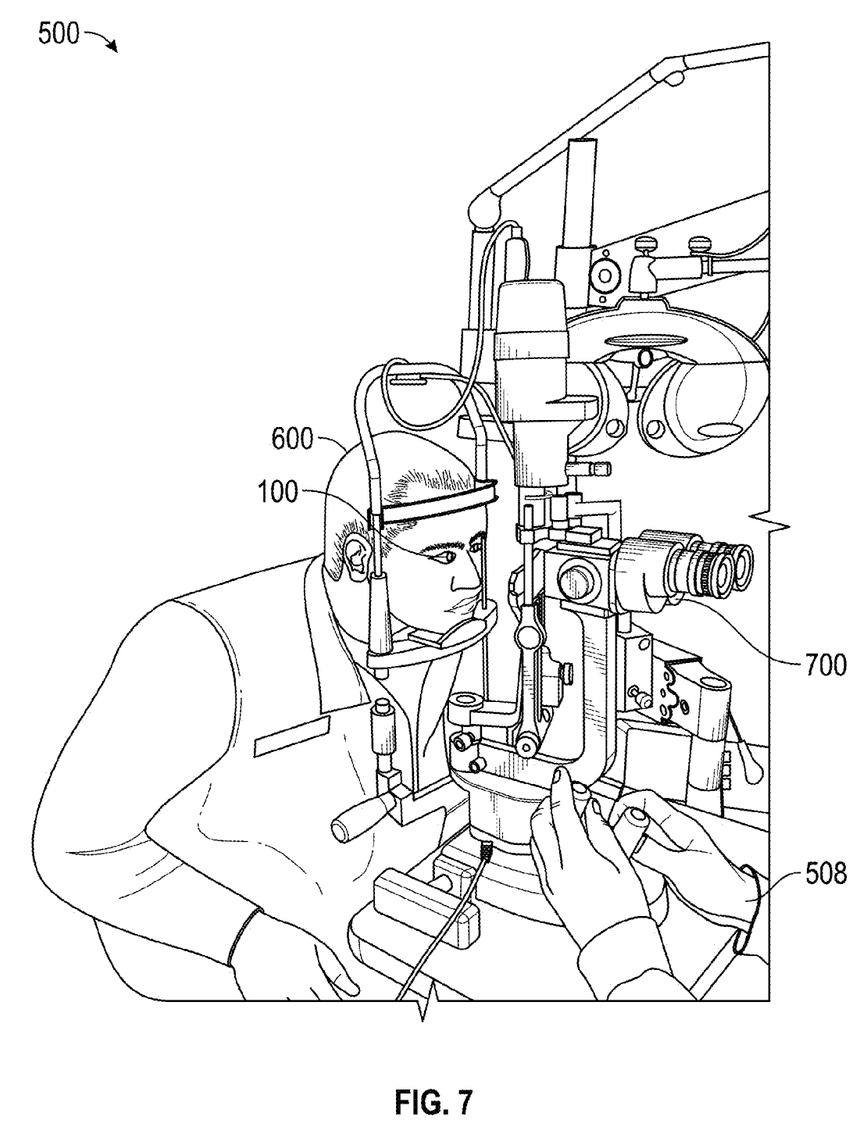
FIG. 7 is a perspective view of the examiner using the eye examination template of FIG. 3 on the patient with an eye examination instrument that is a slit lamp.

Referring to FIGS. 5-7, a system 500 for examining the optic disc 108 of the eye 100 of a patient 600 is shown. Generally, the system 500 can comprise an eye examination instrument configured to view the fundus of the eye 100 and the eye examination template 300. Referring to FIGS. 5-6B, in one aspect, the eye examination instrument can be an ophthalmoscope 502. Generally, the ophthalmoscope 502 can comprise an aperture wheel 504 in which the eye examination template 300 can be positioned. An illumination source 506 can direct light through the eye examination template 300 in the aperture wheel 504 and be reflected into the patient's eye 100 such that the eye examination template 300 is projected onto the fundus of the eye 100. FIG. 6A shows the eye examination template 300 projected on a wall behind a patient, illustrating the use of an illumination source 506 to project the eye examination template 300 from the ophthalmoscope 502. When the eye examination template 300 is projected onto the fundus of the eye by an eye specialist or examiner 508 as shown in FIGS. 5 and 6B, the examiner 508 can view the fundus of the eye 100, and accordingly the projection of the eye examination template 300 on the fundus of the eye 100, through an opening 510 of the ophthalmoscope 502. Optionally, the examiner 408 can utilize a lens wheel 512, which can comprise various types of lenses 514, to bring the image of the funds of the eye 100 into focus. In one aspect, the examiner 508 can use various lenses 514 until the focus circles 316 of the eye examination template 300 are in focus. Referring to FIG. 7, in another aspect, the eye examination instrument can be a slit lamp 700. It is contemplated that various other eye examination instruments capable of viewing the fundus of the eye 100 can be present and can be used with the eye examination template 300.

In other aspects, the eye examination template 300 can be effectively projected on the eye 100 from the view of the examiner 508 without using an illumination source 506 directing light through the eye examination template by placing the eye examination template 300 on a lens through which the examiner 508 views the eye 100, such as on the lenses 514. The eye examination template 300 can thereby be positioned over the fundus of the eye 100 from the view of the examiner 508 without directly projecting the eye examination template 300 onto the fundus of the eye 100 with the illumination source 506. The eye examination template 300 can also be used in conjunction with a retinal camera to overlay the eye examination template 300 digitally or with a lens over a photograph of the fundus of the eye 100, or by taking a photograph of the eye examination template 300 directly projected on the eye 100.

A method of examining the optic disc 108 and the cup 112 of the eye 100 of the patient 600 is disclosed. In one aspect, the examiner 508 can request the patient 600 to put their head in a normal position in front of the eye examination template 300, such as the slit lamp 700, a retinal camera or other device, or the ophthalmoscope 502, or the examiner 508 can bring the eye examination template 300 into position in front of the eye 100 of a seated or otherwise non-moving patient 600. In one aspect, the patient 600 putting their head in the normal position can include having the patient 600 look into the distance or at a point designated by the examiner 508.

In one aspect, the method can comprise projecting the eye examination template 300 directly or effectively on the fundus of the eye 100 of the patient 600. The method can comprise the examiner 508 looking at the fundus of the eye 100 via the eye examination instrument. In one aspect, the method can comprise aligning the first optic disc oval 308 of the eye examination template 300 on the optic disc 108 of the eye 100. In this aspect, aligning the first optic disc oval 308 can further comprise centering the intersection 306 of the x-axis measurement line 302 with the y-axis measurement line 304 on a center of the optic disc 108 or positioning one or multiple edges of the optic disc 108 over an edge of the first optic disc oval 308 or any other position to allow measurement of a difference in size between the first optic disc oval 308 and the optic disc 108. In another aspect, the method can comprise aligning the second optic disc oval 310 of the eye examination template 300 on the optic disc 108.

Optionally, in another aspect, the method can comprise measuring the optic disc 108 with the x-axis measurement marks 312 on the x-axis measurement line 302 of the eye examination template 300. The method can further comprise measuring the optic disc 108 with the y-axis measurement marks 314 on the y-axis measurement line 304 of the eye examination template 300. Optionally, in a further aspect, the method can comprise measuring the cup 112 with the x-axis measurement marks 312 on the x-axis measurement line 302 of the eye examination template 300. The method can further comprise measuring the cup 112 with the y-axis measurement marks 314 on the y-axis measurement line 304 of the eye examination template 300. In these aspects, the method can further comprise calculating a cup-to-disc ratio based on the measurements with the x-axis measurement marks 312 and the y-axis measurement marks 314.

Optionally, in a further aspect, the method can comprise comparing the optic disc 108 to the first optic disc oval 308. Alternatively, the method can comprise comparing the optic disc 108 to the second optic disc oval 310. In one aspect, the method can comprise comparing the optic disc 108 to one of the first optic disc oval 308 and the second optic disc oval 310 based on a demographic of the patient 600 and the corresponding demographic associated with the first optic disc oval 308 and the second optic disc oval 310.

In yet another aspect, the method can comprise focusing the eye examination template 300 on the fundus of the eye 100 by bringing a focus circle 316 of the eye examination template 300 into focus.

In one aspect, the optic disc ovals 308,310 of the eye examination template 300 can provide fixed references to which an examiner 508 can compare the examined optic disc 108 such that the examiner 508 can document any abnormalities or changes from the average normal for a particular demographic. For example and without limitation, the eye examination template 300 can enable the examiner 508 to measure a percentage increase or percentage decrease in the optic disc 108 relative to the first optic disc oval 308 or the second optic disc oval 310 through the measurement marks 312,314, respectively. As another non-limiting example, the eye examination template 300 can enable the examiner 508 to measure a change in shape of the optic disc 108 relative to the first optic disc oval 308 or the second optic disc oval 310.

In another aspect, the eye examination template 300 can enable the examiner 508 to quantify a size of the optic disc 108, a size of the cup 112, or both, through the measurement marks 312,314, respectively. In yet another aspect, the eye examination template 300 can enable the examiner to quantify the size of the optic disc 108 and the cup 112 to quantify the cup-to-disc ratio for the eye 100. The quantifications of the size of the optic disc 108 and the size of the cup 112 can be relevant in the assessment of the health of the eye 100. For example, the quantification of the cup-to-disc ratio through the eye examination template 300 can be used to observe and diagnose various medical conditions. The cup-to-disc ratio is a function of the size of the optic disc. Once established, the optic disc size typically remains constant. There is also an accepted demographic variation in acceptable cup-to-disc ratios. For example and without limitation, some studies have indicated that a cup-to-disc ratio from between about 0.4 to about 0.8 can indicate a normal optic disc 108 while a cup-to-disc ratio greater than about 0.8 can indicate glaucoma, although these ratios can vary by demographics. As another non-limiting example, some studies have indicated that a difference greater than about 0.2 between the cup-to-disc ratios in each of a patient's eyes can indicate an early sign of glaucoma. In yet another aspect, the eye examination template 300 can be utilized to measure lesions on the retina 106 via the measurement marks 312, 314, respectively.

The presence of optic disc ovals 308,310 also permit the examiner 508 to make an initial comparison between the patient 600 and the average person of his or her demographic. This allows the examiner 508 to be alerted to possible diagnoses to be aware of and watch for upon continued monitoring of the patient 600 through routine check-ups, for instance. For example and without limitation, if the size of the patient 600's optic disc 108 or the patient 600's cup-to-disc ratio is noticeably larger than a one of the disc ovals 308,310 corresponding with his or her demographic, the examiner 508 is thereby alerted that the patient 600 may have glaucoma.

It should be emphasized that the above-described aspects are merely possible examples of implementations, merely set forth for a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims which follow, they are used only in a generic and descriptive sense, and not for the purposes of limiting the described invention, nor the claims which follow.

That which is claimed is:

1. An eye examination template for measuring an optic disc comprising:
    an x-axis measurement line comprising a plurality of x-axis measurement marks, each one of the plurality of x-axis measurement marks spaced apart at a first distance from an adjacent one of the plurality of x-axis measurement marks;
    a y-axis measurement line intersecting the x-axis measurement line at a square angle intersection, the y-axis measurement line comprising a plurality of y-axis measurement marks, each one of the plurality of y-axis measurement marks spaced apart at a second distance from an adjacent one of the plurality of y-axis measurement marks; and
    an optic disc oval centered on the intersection of the y-axis measurement line with the x-axis measurement line, the optic disc oval corresponding with an average optic disc size of a first demographic of a population.

2. The eye examination template of claim 1, wherein the optic disc oval is an inner optic disc oval, the eye examination template further comprising an outer optic disc oval centered on the intersection of the y-axis measurement line and the x-axis measurement line and surrounding the inner optic disc oval, the outer optic disc oval corresponding with an average optic disc size of a second demographic of the population.

3. The eye examination template of claim 2, wherein the first demographic is Caucasian and the second demographic is African-American.

4. The eye examination template of claim 2, wherein the first demographic is female and the second demographic is male.

5. The eye examination template of claim 1, wherein the optic disc oval is a one of a plurality of optic disc ovals centered on the intersection of the y-axis measurement line with the x-axis measurement line, wherein each of the plurality of optic disc ovals corresponds with a different demographic of the population.

6. The eye examination template of claim 1, wherein the x-axis measurement line comprises ten x-axis measurement marks, and wherein the y-axis measurement line comprises ten y-axis measurement marks.

7. The eye examination template of claim 6, wherein the x-axis measurement line comprises five x-axis measurement marks in a first direction from the intersection with the y-axis measurement line and five x-axis measurement marks in a second direction from the intersection with the y-axis measurement line, and wherein the y-axis measurement line comprises five y-axis measurement marks above the intersection with the x-axis measurement line and five y-axis measurement marks below the intersection with the x-axis measurement line.

8. The eye examination template of claim 1, further comprising a focus circle configured to indicate when the eye examination template is focused over the optic disc.

9. The eye examination template of claim 1, further comprising a plurality of focus circles configured to indicate when the eye examination template is focused over the optic disc, wherein:
    a first one of the plurality of focus circles is positioned at the intersection of the y-axis measurement line and the x-axis measurement line;
    a second one of the plurality of focus circles is positioned on the x-axis measurement line proximate a first end of the x-axis measurement line;
    a third one of the plurality of focus circles is positioned on the x-axis measurement line proximate a second end of the x-axis measurement line;
    a fourth one of the plurality of focus circles is positioned on the y-axis measurement line proximate a first end of the y-axis measurement line; and
    a fifth one of the plurality of focus circles is positioned on the y-axis measurement line proximate a second end of the y-axis measurement line.

10. The eye examination template of claim 1, wherein:
    the x-axis measurement line comprises a first end and a second end;
    the y-axis measurement line comprises a first end and a second end; and
    each of the first end of the x-axis measurement line, the second end of the x-axis measurement line, the first end of the y-axis measurement line, and the second end of the y-axis measurement line extend from the intersection of the y-axis measurement line with the x-axis measurement line beyond a perimeter of the optic disc oval.

11. A system for examining an optic disc of an eye comprising:
    an eye examination instrument configured to view a back of the eye; and
    an eye examination template configured to be projected onto the back of the eye through the eye examination instrument, the eye examination template comprising
    an x-axis measurement line,
    a y-axis measurement line intersecting the x-axis measurement line at a square angle intersection, and an optic disc oval centered on the intersection of the y-axis measurement line with the x-axis measurement line, the optic disc oval corresponding with an average optic disc size of a first demographic of a population.

12. The system of claim 11, wherein the optic disc oval is an inner optic disc oval, and wherein the eye examination template further comprises:
an outer optic disc oval centered on the intersection of the y-axis measurement line and the x-axis measurement line and surrounding the inner optic disc oval, the outer optic disc oval corresponding with an average optic disc size of a second demographic of the population.

13. The system of claim 11, wherein the eye examination instrument is an ophthalmoscope.

14. The system of claim 11, wherein the eye examination instrument is a slit lamp.

15. The system of claim 11, wherein:
the x-axis measurement line comprises a plurality of x-axis measurement marks, each one of the plurality of x-axis measurement marks spaced apart at a first distance from an adjacent one of the plurality of x-axis measurement marks; and
the y-axis measurement line comprises a plurality of y-axis measurement marks, each one of the plurality of y-axis measurement marks spaced apart at a second distance from an adjacent one of the plurality of y-axis measurement marks, wherein the second distance is greater than the first distance.

16. A method of examining an optic disc and a cup of an eye of a patient, the method comprising:
projecting an eye examination template on a back of the eye, the eye examination template comprising an x-axis measurement line and a y-axis measurement line intersecting the x-axis measurement line at a square angle intersection; and
aligning an optic disc oval of the eye examination template on the optic disc of the eye, the optic disc oval centered on the eye examination template on the intersection of the y-axis measurement line with the x-axis measurement line, the optic disc oval corresponding with an average optic disc size of a first demographic of a population.

17. The method of claim 16, further comprising:
measuring the optic disc with x-axis measurement marks on the x-axis measurement line and with y-axis measurement lines on the y-axis measurement line;
measuring the cup with the x-axis measurement marks on the x-axis measurement line and with the y-axis measurement lines on the y-axis measurement line; and
calculating a cup-to-disc ratio.

18. The method of claim 16, further comprising:
measuring the optic disc with x-axis measurement marks on the x-axis measurement line and with y-axis measurement lines on the y-axis measurement line; and
comparing the optic disc to the optic disc oval.

19. The method of claim 16, wherein the optic disc oval is an inner optic disc oval, wherein the eye examination template further comprises an outer optic disc oval centered on the intersection of the y-axis measurement line and the x-axis measurement line and surrounding the inner optic disc oval, wherein the outer optic disc oval corresponds with an average optic disc size of a second demographic of the population, and wherein the method further comprises:
comparing the optic disc to at least one of the inner optic disc oval and the outer optic disc oval based on a demographic of the patient.

20. The method of claim 16, further comprising:
focusing the eye examination template on the back of the eye by bringing a focus circle on the eye examination template into focus.

* * * * *